(12) United States Patent
Sinko et al.

(10) Patent No.: US 9,211,358 B2
(45) Date of Patent: Dec. 15, 2015

(54) DRESSING COMPOSITIONS AND METHODS

(75) Inventors: Patrick J. Sinko, Lebanon, NJ (US);
Stanley Stein, East Brunswick, NJ (US);
Anupa R. Menjoge, Highland Park, NJ (US); Simi Gunaseelan, Highland Park, NJ (US); Siva Naga Sree Priay Anumolu, Morris Plains, NJ (US);
Raghavandra Navath, Detroit, MI (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 1451 days.

(21) Appl. No.: 12/450,995

(22) PCT Filed: Apr. 23, 2008

(86) PCT No.: PCT/US2008/005246
§ 371 (c)(1),
(2), (4) Date: Oct. 27, 2010

(87) PCT Pub. No.: WO2008/133918
PCT Pub. Date: Nov. 6, 2008

(65) Prior Publication Data
US 2011/0033503 A1    Feb. 10, 2011

Related U.S. Application Data

(60) Provisional application No. 61/925,910, filed on Apr. 24, 2007.

(51) Int. Cl.
| | |
|---|---|
| A61K 47/30 | (2006.01) |
| A61P 17/02 | (2006.01) |
| A61K 38/18 | (2006.01) |
| A61K 38/06 | (2006.01) |
| A61L 15/22 | (2006.01) |
| A61L 26/00 | (2006.01) |
| A61L 15/26 | (2006.01) |
| A61L 15/44 | (2006.01) |

(52) U.S. Cl.
CPC ............ *A61L 26/0076* (2013.01); *A61L 15/26* (2013.01); *A61L 15/44* (2013.01); *A61L 2300/25* (2013.01); *A61L 2300/402* (2013.01); *A61L 2300/404* (2013.01); *A61L 2300/41* (2013.01); *A61L 2300/414* (2013.01); *A61L 2300/602* (2013.01)

(58) Field of Classification Search
None
See application file for complete search history.

(56) References Cited

U.S. PATENT DOCUMENTS

| | | | |
|---|---|---|---|
| 6,514,535 B2 * | 2/2003 | Marchant | 424/486 |
| 6,565,842 B1 | 5/2003 | Sojomihardjo et al. | |
| 6,818,018 B1 * | 11/2004 | Sawhney | 623/11.11 |
| 2003/0166833 A1 * | 9/2003 | Lutolf et al. | 530/300 |
| 2005/0196696 A1 | 9/2005 | King | |
| 2005/0256030 A1 * | 11/2005 | Feng | 514/2 |
| 2006/0140918 A1 | 6/2006 | Tresco et al. | |
| 2008/0253987 A1 * | 10/2008 | Rehor et al. | 424/78.37 |

OTHER PUBLICATIONS

-thiol, Hawley's Condensed Chemical Dictionary, 14th ed. (2002).*
Written Opinion of the International Searching Authority and International Search Report issued in connection with corresponding International Application No. PCT/US2008/005246.
International Search Report issued in connection with International Patent Application No. PCT/US2008/005246.

* cited by examiner

*Primary Examiner* — H. Sarah Park
(74) *Attorney, Agent, or Firm* — Fox Rothchild LLP

(57) ABSTRACT

Described is a spray-on hydrogel comprising water-soluble PEG polymers that cross-link in situ to form a hydrogel such that the cross-links are reversible. The hydrogel can be useful as a drug delivery composition, wound dressing or surgery adjuvant. Polyethylene glycol polymer and cross-linker solutions are sprayed simultaneously through a common orifice. Cross-linking via formation of thioether or disulfide bonds is initiated upon mixing, providing rapid gelation. The hydrogel components can be derivatized with RGD peptides or analogs thereof to promote retention in/on a body compartment such as the skin, surface of the eye, or a mucosa such as the vaginal mucosa. The cross-links are reversed using a reducing solution enabling easy removal of the hydrogel by dissolution. Processes for preparation of the cross-linker, RGD derivatized PEG and RGD-linked agents are also disclosed.

35 Claims, 4 Drawing Sheets

Figure 1. Formation of disulfide bridges (cross-links) leading to hydrogel based on 8-armPEG-SH and 8-armPEG-S-TP (thiopyridine).
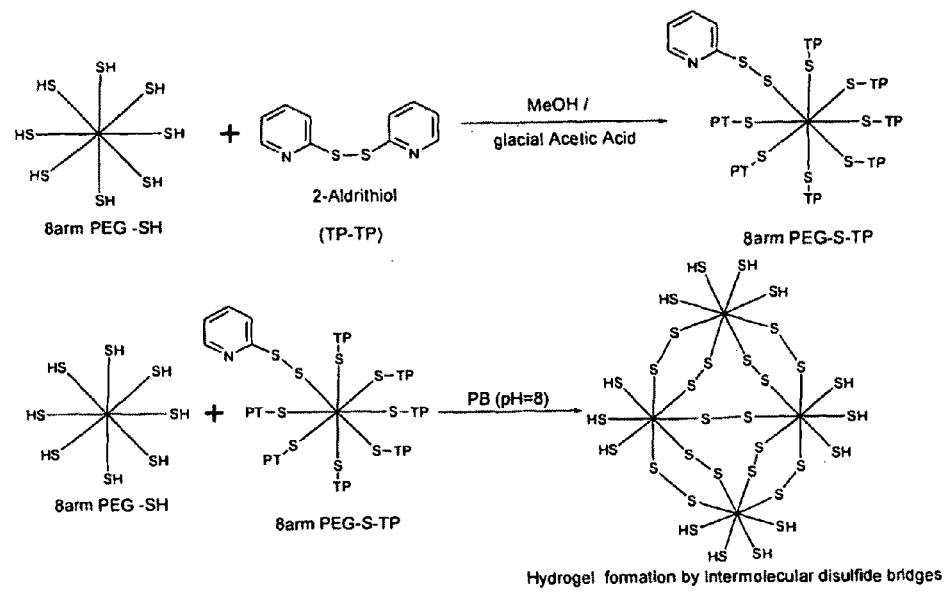
Figure 2. Formation of disulfide bridges (cross-links) leading to hydrogel based on 4-armPEG-SH and 4-armPEG-S-TP (thiopyridine).
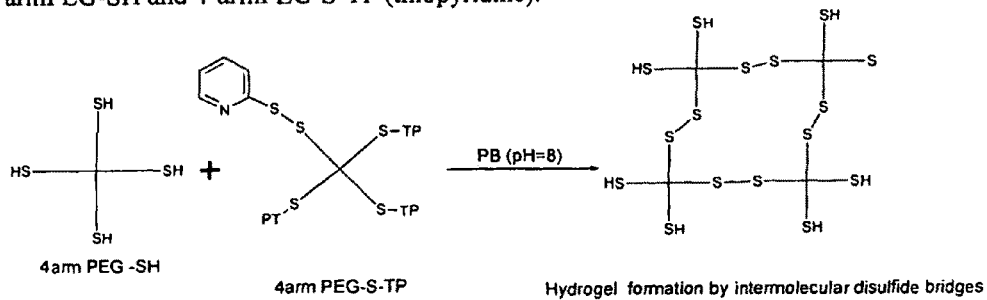
Figure 3. Formation of disulfide bridges (cross-links) leading to hydrogel based on 8-armPEG-SH and 4-armPEG-S-TP (thiopyridine).

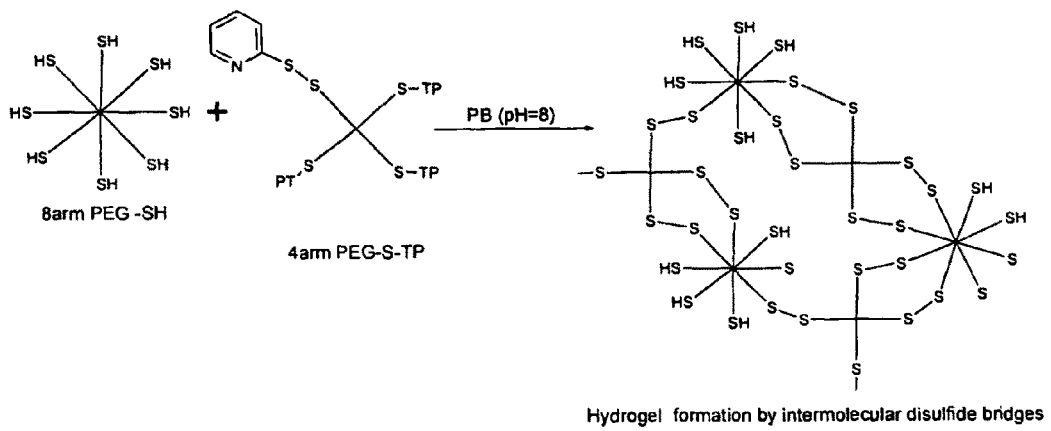
Figure 4. Formation of disulfide bridges (cross-links) leading to hydrogel based on 4-armPEG-SH and 8-armPEG-S-TP (thiopyridine).
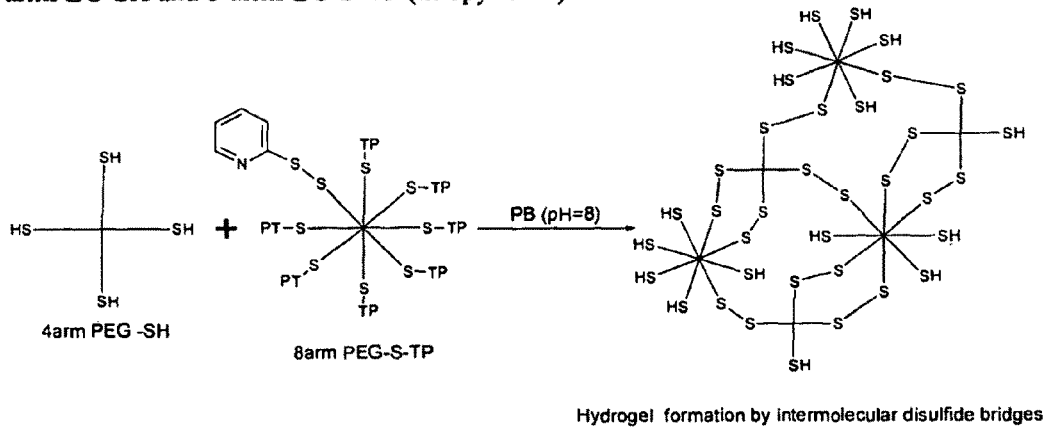
Figure 5. Formation of disulfide bridges (cross-links) leading to hydrogel based on 4-armPEG-SH and $H_2O_2$
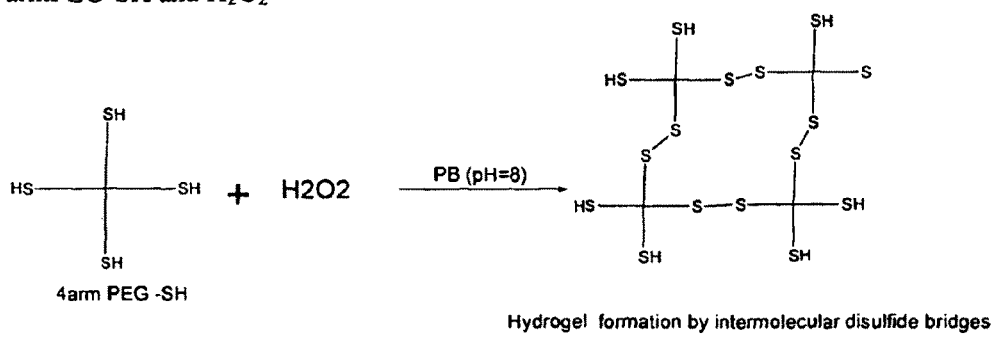

Figure 6. Formation of disulfide bridges (cross-links) leading to hydrogel based on 8-armPEG-SH and $H_2O_2$
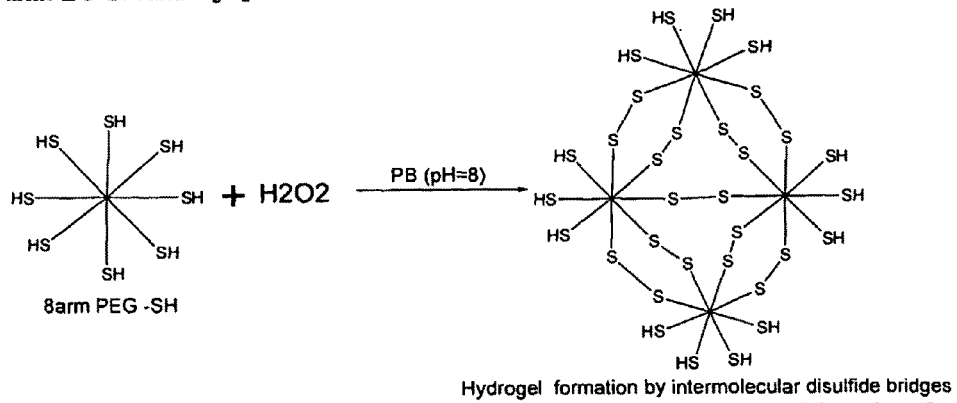
Figure 7. Formation of thioether bonds (cross-links) leading to hydrogel based on 8-armPEG-SH and $BMPEO_3$
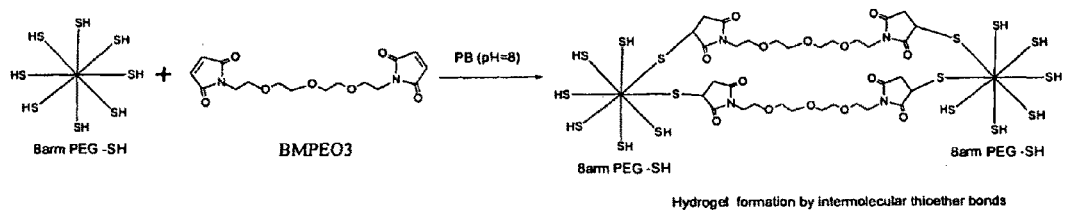
Figure 8. Formation of thioether bonds (cross-links) leading to hydrogel based on 8-armPEG-SH and $BMPEO_2$
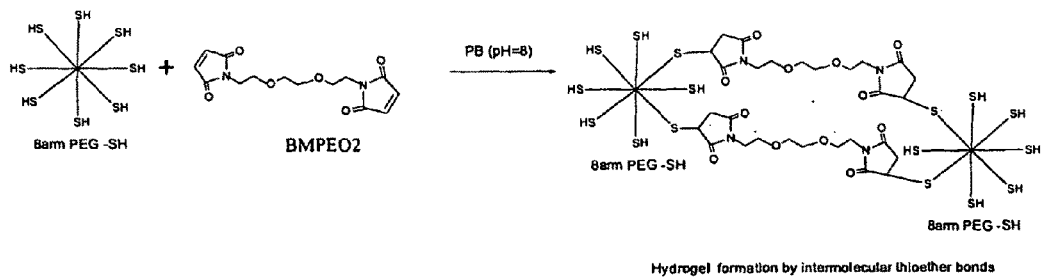

Hydrogel formation on Petri dish and a dual barrel syringe for application of the hydrogel polymer and cross-linker.

Attaching the RGD peptide on the 8-arm-Peg-SH

DRESSING COMPOSITIONS AND METHODS

CROSS REFERENCE TO RELATED APPLICATIONS

The present application is the U.S. National Phase of International Patent Application Serial No. PCT/US08/05246, filed Apr. 23, 2008, which claims the benefit of U.S. Provisional Patent Application Ser. No. 60/925,910, filed Apr. 24, 2007. The contents of the foregoing applications are hereby incorporated by reference in their entireties.

BACKGROUND OF THE INVENTION

The use of hydrogel-based wound dressings for the promotion of wound healing is accepted clinical practice for wounds that have low to medium exudate. These dressings are typically applied to the skin as an adhesive bandage. Hydrogel-based wound dressings are cross-linked polymer gels in sheet form, having a gauze or an impervious polymer backing with an adhesive component provided for skin adhesion. Examples include, hydropolymer dressings impregnated with petroleum gauze or having water-resistant permeable polyurethane backing, paste dressings containing zinc oxide and calamine, waterproof foam dressing made of polyurethane film, guaze-based stretchable dressing, alginate-based dressings, collagen-based dressings and silver dressings. Hydrogel sheets are available from several commercial sources, including Tegagel (3M), Vigilon (Bard), Clearsite (Conned Corporation), AQUASORB (DeRoyal), FLEX-DERM (Bertek), NU-GEL (Johnson & Johnson), and CURAGEL (Kendall). These adhesive gauze or patch products, however, remain intact and have the disadvantage of being difficult to remove when peeling off from the skin.

Hydrogels have also been employed to increase ocular residence time and enhance bioavailability for drugs applied to the eye. The hydrogels were found to provide better tolerability and less blurring of vision than ointments. Hydrogels used for ocular application are either pre-formed gels or are formed in situ. The pre-formed gels comprise, for example, cellulose derivatives, such as hydroxyethyl cellulose, hydroxymethyl cellulose, carboxymethyl cellulose; polyacrylic acids; cross-linked acrylic acid derivatives (carbomer); polyarcylamides; carbophil; gelatin; hyaluronic acid; polyvinyl alcohol; polyvinyl pyrrolidone; or xanthan gum.

The in situ-forming gels typically comprise cellulose acetate phthalate, polaxomers, ethylene diamine derivative of polaxamine; psuedolatexes prepared by the incorporation of pilocarpine in cellulose acetate phthalate; various copolymers, such as PEO-PLLA and PEG-PLGA-PEG; cellulose acetophalate latex; Gelrite; carbopol; Matrigel; polyethylene oxide, polyoxypropylene, or gellan gum. However, most require a high (>20%) polymer concentration for in situ gel formation. Thermally gelling polymers (Poloxamer, Pluronics, PEO-PLLA diblock copolymer, PEG-PLGA-PEG triblock copolymer, and Matrigel) have a disadvantage of gelling before administration due to temperature change during packaging or storage, and can require manipulation of the temperature before administration. Furthermore, many of these polymers (e.g., Poloxamer and Pluronics) form a hydrogel which is a viscous, but still flowing solution and therefore are not readily applicable for use at a particular site on body surfaces.

An in situ gelling polyvinyl alcohol (PVA)-based, fast cross-linking hydrogel system in the form of a spray, and suitable as a wound dressing, has been disclosed by Bohl Masters, et al., Wound Repair and Regeneration 10 (5), 286-294, 2002; and Bourke, et al., AAPS PharmSci 2003; 5(4) article 33. The PVA is functionalized by reacting with the acrylamide derivatives and are cross-linked by UV irradiation. The hydrogel provides a protective barrier on the skin but the cross-linking is irreversible. Accordingly, these hydrogel systems are not readily soluble and have to be peeled off to be removed them from the site.

BRIEF SUMMARY OF THE INVENTION

A hydrogel which can form in situ and is readily soluble, i.e., has reversible cross-linkage, can provide certain advantages as a wound or ocular dressing or drug delivery device at the site of application. These advantages include being relatively easy and painless to remove from the site of application, as well as being highly conformable to the site of application, such as a wound, the eye, or surrounding tissue. In addition, an in situ-forming hydrogel that can be administered as a spray can provide an advantageous method of application to the site. A spray-on gel for the topical delivery of drug to the eye, and having the drug or drugs linked to RGD peptides, which exhibit adhesive properties, can enhance the ocular residence time for the linked drugs.

The subject invention concerns compositions, drug delivery devices and methods relating to in situ-forming hydrogels useful to form a protective covering over a wound or damaged area of the skin, such as cut or abrasion, a surgical site, or a blistered surface resulting from disease or trauma, such as a burn. An in situ-forming hydrogel composition of the subject invention can also be useful as a carrier for a drug or drugs administered by topical or transdermal application, including ocular application. The hydrogels of the subject invention can be adherent, i.e., the composition, itself, can have adherent or adhesive properties.

Thus, the subject invention concerns a wound or ocular dressing comprising a first component comprising a hydrophilic polymer having a sulfhydryl, thiol, or mercaptan moiety; and a second component comprising a cross-linker, said cross-linker forming reversible cross-linkages with the hydrophilic polymer. The first and second components form a material that adheres to skin of a mammal and acts as a wound dressing. Preferably, the polymer is polyethylene glycol, and more preferably, the polyethylene glycol comprises a sulfhydryl, thiol, or mercaptan moiety to form disulfide bonds. The composition can also include a peptide, such as RGD peptide, the RGD peptide preferably being derivatized to the polyethylene glycol component. The composition can alternatively or additionally include a drug or combination of drugs or a growth factor.

The subject invention also concerns a method of treatment for delivering a drug to a corneal surface of an eye. This method comprises the steps of:

a. providing a reversibly cross-linked hydrogel composition of claim 14, and b. removing the hydrogel by dissolving said cross-links in the hydrogel composition.

Removal of the hydrogel dressing preferably comprises reversing the cross-links using a reducing agent wherein the reducing agent is preferably cysteine or derivatives thereof, cysteine ethyl ester, cysteine methyl ester, gluthatione, cysteine hydrocholoride, dithiothretol, N-Ethylmalemide, phosphine derivatives tetrakis-hydroxymethyl phosphonium chloride and tris-diethylaminomethyl phosphine trialkylphosphine agents, such as Tris[2-carboxyethyl]phosphine and mercaptoethanols, 2,3-dimercapto-1-propanol, dinitrobenzoic acid, a thiol, a mercaptan, a sulfite or bisulfite or ammonium or sodium salts thereof, thioglycolic acid, thiolactic acid, cysteine, thioglycerol, thioglycolic hydrazide, thioglycolamide, glycerol monothioglycolate, beta-mercapto-propionic acid, N-hydroxyethyl mercapto-acetamide, N-methyl mercapto-acetamide, beta-mercapto-ethylamine, beta-mercapto-propionamide, 2-mercapto-ethanesulfonic acid, dimercapto-adipic acid, dithiothreitol, homocysteinethiolactone, and a polythiol derivative formed by the addition of cysteamine onto a maleic anhydride-alkylvinylether copolymer, and is most preferably glutathione or cysteine.

The subject invention further includes a method of preparing a cross-linked hydrogel composition for application to the skin, said method comprising:

a. providing a polymer in solution,
b. providing in a separate solution a cross-linker that forms reversible cross-links,
c. administering both solutions concomitantly from at least one nozzle permitting mixing of the polymer and cross-linking solutions in order to provide rapid gelation of the reversibly cross-linked hydrogel at the site of administration.

A preferred embodiment of a composition of the subject invention comprises novel cross-linkers, such as RGD-derivatized PEG, and further can comprise RGD-linked drug. A hydrogel composition of the subject invention can comprise additional components or ingredients, including polyvinylpyrrolidone (PVP), propylene glycol, low molecular weight PEG (<6000 Da), glycerin, or cellulose derivatives such as hydroxypropyl cellulose, hydroxylpropyl methylcellulose, methythellulose, or the like, as necessary to provide desired properties for the hydrogel in accordance with the functionalities as recognized in the art.

The polymeric PEG component of the subject composition preferably comprises a sulfhydryl, thiol, or mercaptan moiety capable of forming a reversible disulfide bond or bridge for cross-linkage of the polymer. A preferred composition of the hydrogel according to the subject invention comprises a thiol-terminated PEG and several substances that are useful for cross-linking the thiol groups. Alternately, a PEG having a maleimide, thiopyridine or vinylsulfone termination can be used. At physiological pH and temperatures, cross-linking of PEG into a hydrogel can occur in about 1-3 minutes. The use of PEG offers several other advantages, including its chemoselective properties, its capability to form reversible and non-reversible cross-links, its free thiol group for covalently linking to drug, its property of blocking proteolytic enzymes and immune system components that can cause an inflammatory reaction, and its commercial availability in numerous forms.

More preferably, the sulfhydryl or thiol or mercaptan-terminated PEG can reversibly bond to a sulfur-terminated moiety of a peptide, such as a peptide comprising the amino acid chain Arg-Gly-Asp (RGD) or a sulfur-containing amino acid, such as Cys. Thus, one preferred peptide used in accordance with the subject invention comprises Cys attached to the Asp amino acid of the RGD peptide. Use of a PEG-based polymer allows the hydrogel to be functionalized using these peptides to enhance the wound healing and the adhesive properties of the gel. Peptides typically used for this purpose include those having the sequence 'Arg-Gly-Asp,' or RGD, in cyclic or linear form. The heretofore undisclosed PEG polymers derivatized to include RGD peptide useful as cross-linker in a spray-on gel can advantageously provide bioadhesive and wound-healing properties to the formed hydrogel.

In a preferred wound dressing embodiment of the subject invention, the PEG and cross-linker can be provided as separate solutions, being mixed during administration to the site, for example, provided as streams of solutions from separate sources or containers and administered simultaneously, allowing the gel and cross-linker solutions to mix together during administration, so that the cross-linked gel matrix sets in less than 30 minutes, and preferably less than 10 minutes. The disulfide bonds of the resultant cross-linked hydrogel matrix can provide the support to maintain the integrity of the gel, as well as the capability to adsorb into the gel the exudate from the wound or other site. The cross-linking within the polymeric composition can be readily reversed using a reducing agent. Such spray-on hydrogels having reversible cross-links for advantageous application to skin have not been previously disclosed. A preferred object of the invention is to provide enhanced patient compliance for a wound dressing by applying a hydrogel having reversible cross-links, e.g., cross-links containing disulfide bridges, so that the hydrogel wound dressing can be readily washed off by dissolution of the hydrogel rather than physical removal, such as peeling off, of the intact dressing.

The drugs and other active components used in accordance with the subject invention can be dissolved or dispersed in the cross-linked polymeric matrix. Drugs which can provide anesthetic, antimicrobial, or wound healing properties are preferred for use in an embodiment directed to a protective covering for a wound. Alternatively, the drugs can be linked to an RGD peptide derivatized onto the PEG polymer.

Another feature of the present invention is that hydrogel, cross-linked with RGD derivatized PEG cross-linker, can provide dermal retentive properties when applied to the skin, thereby providing prolonged release properties for the drug released from the hydrogel. This embodiment of a hydrogel of the subject invention can also enhance the cell adhesion of the drugs onto a corneal surface.

The subject invention preferably comprises a hydrogel which is formulated to be applied or administered, preferably as a liquid and more preferably as a spray, wherein the formed gel comprises a reversibly cross-linked polymeric matrix or network. The cross-linking component is also preferably formulated as a liquid and more preferably as a spray. The hydrogel and cross-linking components are therefore preferably applied concomitantly as separate liquids and more preferably administered as a spray wherein the two liquids are mixed during the application thereof.

By comprising a reversible cross-link, the hydrogel is soluble, and can be dissolved and easily removed from the site rather than requiring the gel to be removed intact, e.g., peeled, from the skin. More preferably, the spray formulation for the gel of the subject invention comprises cross-linked, water-soluble polyethylene glycol (PEG) polymers. PEG is advantageously a hydrogel-forming component that is well known for its safe and non-toxic properties.

It is yet another object of the present invention to provide a rapidly gelling hydrogel network which can be sprayed into the eye to treat inflammation, allergic response or to treat infection. Further, the spray gel can be applied onto a wound or other traumatized area of the skin to aid the healing process. Preferably, gelation should occur in less than 30 minutes, more preferably within about 10 minutes, and most preferably in less than about 4 minutes. It is still another object of the invention to provide an in situ-forming hydrogel which results in gelation in less than one minute.

It is another object of the present invention to provide a spray-on hydrogel system comprising a dual-source nozzle, such as a dual barrel syringe or a pressurized spray can, capable of concomitant spraying of a stream of polymeric solution and a stream of cross-linker solution. This spray-on hydrogel system can provide advantageous topical delivery to the eye or skin of an in situ-forming hydrogel containing a drug or drugs.

A further object of the invention is to provide a controlled-release drug delivery system comprising a hydrogel wherein the drug or drugs are delivered from or through the hydrogel composition for a sustained or extended period of time. Preferably, the drug or drugs can be linked to RGD peptides incorporated into a PEG-based hydrogel. Linkage of drug to the RGD peptide component of the hydrogel can increase residence time in the ocular region or on the skin cells to increase their residence time at the site of application, thereby providing relatively high local concentrations and prolonged release and action of the drug or drugs.

Yet another object of the invention is to provide a kit for applying a wound or ocular dressing or a hydrogel capable of delivering drug to the site of application. The kit can comprise a polymer-forming composition and a reversible cross-linking composition, wherein the polymer-forming and cross-linking compositions can be mixed to form a reversible, cross-linked hydrogel which rapidly gels to form a wound dressing or drug delivery device at the site of application. The kit can also include a composition containing drug, growth factor or other wound-healing enhancer, either separate from the polymer-forming composition and the cross-linking composition, or drug can be incorporated into either of these compositions. In addition, the kit can comprise a separately contained reducing agent to reverse the cross-linkage of the formed hydrogel, thereby providing a means for dissolving the hydrogel for its easy removal from the site without having to remove the hydrogel intact.

BRIEF DESCRIPTION OF THE DRAWINGS

FIG. 1 depicts formation of disufide bridges (cross-links) leading to hydrogel based on 8-armPEG-SH and 8-armPEG-S-TP (thiopyridine).

FIG. 2 depicts formation of disufide bridges (cross-links) leading to hydrogel based on 4-armPEG-SH and 4-armPEG-S-TP (thiopyridine).

FIG. 3 depicts formation of disufide bridges (cross-links) leading to hydrogel based on 8-armPEG-SH and 4-armPEG-S-TP (thiopyridine).

FIG. 4 depicts formation of disufide bridges (cross-links) leading to hydrogel based on 4-armPEG-SH and 8-armPEG-S-TP (thiopyridine).

FIG. 5 depicts formation of disufide bridges (cross-links) leading to hydrogel based on 4-armPEG-SH and $H_2O_2$ FIG. 6 depicts formation of disufide bridges (cross-links) leading to hydrogel based on 8-armPEG-SH and $H_2O_2$.

FIG. 7 depicts formation of thioether bonds (cross-links) leading to hydrogel based on 8-armPEG-SH and $BMPEO_3$.

FIG. 8 depicts formation of thioether bonds (cross-links) leading to hydrogel based on 8-armPEG-SH and $BMPEO_2$.

DETAILED DESCRIPTION OF INVENTION

Figure 9:
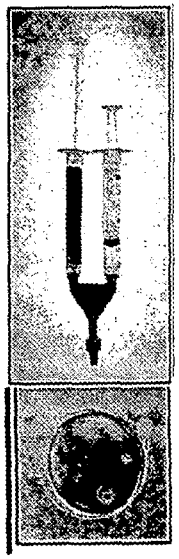
FIG. 9 depicts formation of hydrogel from a dual barrel syringe containing a polymer component and a cross-lining component in the respective barrels.

The subject invention concerns a composition comprising a drug or other active ingredient, a polymeric hydrogel-forming component and a cross-linker, providing in situ formation of the hydrogel when sprayed topically onto an area of the body. The subject hydrogel composition advantageously has bioadhesive properties and reversible cross-links.

A preferred embodiment of the subject composition comprises a polyethylene glycol), or PEG, hydrogel that, when applied topically, provides an adhesive gel which adheres well to a body surface such as the cornea or the skin. Further, the subject composition can provide modulated drug release from the hydrogel so that drug can be released over a prolonged period of time, e.g., several hours or days, or up to about a week. The hydrogel composition of the subject invention preferably comprises RGD peptide-derivatized components, including (a) RGD peptide linked to the PEG to provide cell adhesive and wound-healing properties for the composition, or (b) RGD peptide linked to a drug or drugs used in the compositions to provide increased retention of drug at site of application and for prolonged release of drug to promote or enhance wound healing. By "RGD peptide", it is meant a peptide comprising RGD.

In a preferred use, the polymeric hydrogel and cross-linker are formulated as separate solutions and concomitantly introduced, e.g., sprayed, onto the target site such that the polymer and cross-linker solutions adequately mix to form in situ a cross-linked hydrogel network or matrix. Active drug or drugs can be incorporated into one or both of the solutions, and are preferably linked to the hydrogel forming polymer through an RGD peptide linkage wherein the RGD peptide is incorporated or derivatized into the polymer. The cross-linked hydrogel so formed can provide a protective barrier on an injured or affected area, thereby serving as a wound dressing, or can provide a composition for topical drug delivery.

Preferably, the hydrogel base comprises PEG (polyethylene glycol) or PEG derivatives. A hydrogel formed from PEG is advantageously flexible, elastic and strong, enabling attachment on the eye, skin and or injured parts thereof. In addition, certain derivatized PEGs, such as PEGs derivatized with an RGD peptide, can enhance wound healing, anchor onto the injured site and deliver the drugs for extended periods of time ranging from hours, to days, or up to about a week. A PEG-based hydrogel is highly permeable, allowing diffusion of incorporated drugs, salts, water and gases. Satisfactory gel formation can be achieved using a ratio of polymer to cross-linker from about 5:1 to about 1:5. The concentration of PEG can be varied from about 2% to about 30% (w/w) in the hydrogel, and in certain embodiments is preferably about 8% to about 10%. The polymer and cross-linker are preferably dissolved in buffer in the pH range 4-9 and preferably in the pH range 5-8 to obtain the gels.

The hydrogel composition, such as PEG-based composition, can provide a platform technology suitable for use with various types of drugs to be delivered. The drugs can be either physically entrapped or modified drugs with cleavable bonds can be physically incorporated or covalently linked into the hydrogel to provide controlled release, which is otherwise not possible for highly hydrophilic drugs which traverse easily through the gel.

A composition according to the present invention can also be applied to skin for burns associated with fire, sunburn and chemical irritants, as well as physical injuries such as bed sores by providing a scaffold for seeding and repair of the damaged skin. A distinctive feature of the hydrogel of the subject invention is the formulation of reversible cross-linking such that the hydrogel matrix can be dissolved and readily washed off. This feature can advantageously minimize disruption of newly formed skin when removing the reversibly cross-linked hydrogel dressing, offering advantages over the typical gel bandages, which are required to be physically removed intact, e.g., by peeling off of the dressing, which can cause discomfort or further trauma to the wound site.

The hydrogel composition can further comprise one or more drugs for delivering drug for treatment at the site. The drug or drugs can be physically entrapped within the matrix of the formed hydrogel or can be covalently linked to hydrogel, such as by the RGD peptide. Such drug or drugs can be wound healing enhancers, such as RGD peptides, antiseptics or antibiotics, anti-inflammatories, anesthetics, pain relievers, or drugs useful for in situ treatment, such as drugs for treating glaucoma at an ocular site, and growth factors. These drugs include, but are not limited to lidocaine, benzocaine, butamben, dibucaine, oxybuprocaine, pramoxine, proparacaine, proxymetacaine, novocaine, procaine, tetracaine, doxycycline, minocycline, oxytetracycline, sancycline, dedimethylamino tetracycline, indomethacin, diclofenac, ibuprofen, naproxen, ketoprofen, dexamethasone, a vallinoid, olvanil, capsaicin, benzalkonium chloride, an antiglaucoma medication, pilocarpine, timolol, levobunolol, betaxolol, or carbacol. The invention is not limited to the use of the drugs mentioned above and can be extended to other therapeutic agents which aid in wound healing processes when used for topical skin delivery or drugs used in ocular treatments, such as drugs used to treat glaucoma.

Alternatively, or in addition to comprising a drug or drugs, a hydrogel of the subject invention can include a growth factor for promoting wound healing. The growth factors useful in accordance with the subject invention include the cytokines such as epidermal growth factor (EGF), including all members of the EGF family of proteins having one or more repeats of the conserved amino acid sequence: CX7CX4-5CX10-13CXCX8GXRC (where X represents any amino acid), transforming growth factor alpha (TGF-alpha), Transforming Growth Factor beta (TGF-b), keratinocyte growth factor (KGF-2), fibroblast growth factor fibronectin, fibrinogen, Granulocyte-Monocyte Colony Stimulating Factor (GM-CSF) and platelet-derived growth factor (PDGF).

The subject invention preferably comprises a hydrogel which is formulated to be applied or administered, preferably as a liquid and more preferably as a spray, wherein the formed hydrogel comprises a reversibly cross-linked polymeric matrix or network. By comprising a reversible cross-link, the hydrogel is soluble, and can be dissolved and easily removed from the site rather than requiring the gel to be removed intact, e.g., peeled, from the skin. The cross-linking within the polymeric composition can be readily reversed using a reducing agent. For purposes of the subject invention, substances that have the ability to reduce other substances are said to be reductive and are known as reducing agents, reductants, or reducers. As is well-known in the art, reducing agents can transfer electrons to another substance, and is thereby, itself, oxidized. Because reducing agents "donate" electrons, they are also called electron donors.

The reduction of a typical disulfide bond, as in an embodiment of the subject invention, proceeds by two sequential thiol-disulfide exchange reactions. Thiol-disulfide exchange is the principal reaction by which disulfide bonds are formed and rearranged. Disulfide reshuffling is a faster reaction. Thiol-disulfide exchange is a chemical reaction in which a thiolate group S—attacks a sulfur atom of a disulfide bond —S—S—. The original disulfide bond is broken, and its other sulfur atom is released as a new thiolate, carrying away the negative charge. Meanwhile, a new disulfide bond forms between the attacking thiolate and the original sulfur atom. The transition state of the reaction is a linear arrangement of the three sulfur atoms, in which the charge of the attacking thiolate is shared equally. The protonated thiol form —SH is unreactive, i.e., thiols cannot attack disulfide bonds, only thiolates. Typically, the thiolate of a redox reagent such as glutathione or dithiothreitol attacks the disulfide bond.

The several reducing agents that either block or reverse the disulfide bridges forming the cross-linkage in accordance with the subject invention include cysteine, cysteine ethyl ester, and cysteine methyl ester, gluthatione, cysteine hydrocholoride, dithiothretol, N-Ethylmalemide, phosphine derivatives tetrakis-hydroxymethyl phosphonium chloride and tris-diethylaminomethyl phosphine trialkylphosphine agents, such as Tris[2-carboxyethyl]phosphine and mercaptoethanols, 2,3-dimercapto-1-propanol, and dinitrobenzoic acid. The reducing agents appropriate for use in accordance with the subject invention are not limited to these and can be any compound having thiols or mercaptan groups as well as sulfites and/or bisulfites. Mercaptans and thiols which can be used to reverse the disulfide linkages in a reversibly cross-linked hydrogel of the subject invention include thioglycolic acid, thiolactic acid, cysteine, thioglycerol, thioglycolic hydrazide, thioglycolamide, glycerol monothioglycolate, beta-mercapto-propionic acid, N-hydroxyethyl mercapto-acetamide, N-methyl mercapto-acetamide, beta-mercaptoethylamine, beta-mercapto-propionamide, 2-mercaptoethanesulfonic acid, dimercapto-adipic acid, dithiothreitol, homocysteinethiolactone, cysteine derivatives, and polythiol derivatives formed by the addition of cysteamine onto a maleic anhydride-alkylvinylether copolymer. The sulfites and/or bisulfites which can be used are the sodium and ammonium salts.

Preferred reducing agents of the present invention are cysteine or cysteine derivatives and glutathione. Various concentrations of these agents will be effective in degrading the hydrogel matrix. The higher the concentration, the faster the degradation. However, the lowest effective concentration is preferably used in order to minimize adverse tissue reactions.

A hydrogel composition of the present invention is further suitable for application as an ocular gel. A hydrogel composition of the subject invention can comprise an RGD-containing peptide having bioadhesive properties, linked to the polymeric (e.g., PEG) component for enhancing the adhesion to the cells. Further, RGD-linked drugs incorporated in the gels provide prolonged ocular residence times, enhancing the ocular bioavailability of the drugs.

EXAMPLES OF THE PREFERRED EMBODIMENTS, INCLUDING BEST MODE

Examples of the compositions, components thereof, and properties of embodiments of the subject invention are provided hereinbelow

Example 1

Hydrogel Formation

The hydrogel network or matrix composition is obtained by formation of disulfide bridges or formation of thioether bonds in the PEG (polyethylene glycol) having a thiol group (reduced sulfhydryls groups 'SH') at each terminus. The cross-linking of PEG with thiol terminal groups is achieved by reacting the same with $H_2O_2$, maleimide cross-linkers (like bis-maleimido di/triethylene glycol derivatives eg. $BMPEO_2$ (bis-maleimido diethylene glycol) and $BMPEO_3$ (bis-maleimido triethylene glycol) BMOE (Bis-Maleimidoethane), BMH (bismaleimidohexane)) or PEG having a thiopyridine (TP) groups at the terminus or PEG having vinyl sulfone terminal groups or any other compound capable of forming the disulfide or thioether bonds with 'SH' terminated PEGs. The PEG polymers having thiol terminus groups include 2-, 3-, 4-, 8-arm or multiple arm thiol PEGs in the molecular weight range of 2,000 to 100,000 Da. Alternately the hydrogels can be obtained by cross-linking the PEG having a maleimide or thiopyridine terminated groups with compounds having thiol functionality.

A. Thiol-Terminated Polymer and Hydrogen Peroxide Cross-Linker

One of the embodiments of the present invention includes the gels based on thiol terminated PEGs (e.g., 8-arm-PEG-SH) cross-linked with $H_2O_2$. The in situ forming hydrogel was obtained by spraying the solution of the thiol terminated PEG and the cross linker: $H_2O_2$, in phosphate buffer pH 8 from a dual barrel syringe to obtain the hydrogel.

Formulations according to the subject invention, having various concentrations of hydrogel component, mixed with varying volumes of 3% $H_2O_2$ as a cross-linker, and their relatively rapid gelling time, are shown in Tables 1-3.

TABLE 1

Hydrogel (6% w/v) with $H_2O_2$ as cross-linker

| 8 Arm-PEG-SH | pH = 8 PBS Buffer Volume In μL | 3% $H_2O_2$ Volume In μL | Equivalence of $H_2O_2$ for one SH | Excess of $H_2O_2$ | Gelling Time in Sec |
|---|---|---|---|---|---|
| 10 mg | 166 μL | 33.2 μL (0.9 μL $H_2O_2$) | 6.6 | 5.6 | 30 |
| 10 mg | 166 μL | 16.6 μL (0.45 μL $H_2O_2$) | 3.3 | 2.3 | 33 |
| 10 mg | 166 μL | 8.3 μL (0.22 μL $H_2O_2$) | 1.65 | 0.65 | 36 |
| 10 mg | 166 μL | 4.15 μL (0.11 μL $H_2O_2$) | 0.82 | (−0.18) | 40 |

TABLE 2

Hydrogel (3% w/v) with $H_2O_2$ as cross-linker

| 8-arm-PEG-SH | pH = 8 PBS Buffer Volume In μL | 3% $H_2O_2$ Volume In μL | Equivalence of $H_2O_2$ | Excess of $H_2O_2$ | Gelling Time |
|---|---|---|---|---|---|
| 5 mg | 166 μL | 33.2 μL (0.9 μL $H_2O_2$) | 13.2 | 12.2 | 32 Sec |
| 5 mg | 166 μL | 16.6 μL (0.45 μL $H_2O_2$) | 6.6 | 5.6 | 50 Sec |
| 5 mg | 166 μL | 8.3 μL (0.22 μL $H_2O_2$) | 3.3 | 2.3 | 68 Sec |
| 5 mg | 166 μL | 4.15 μL (0.11 μL $H_2O_2$) | 1.65 | 0.65 | 2.4 min |

TABLE 3

Hydrogel (1.5% w/v) with $H_2O_2$ as cross-linker

| 8-arm-PEG-SH | pH = 8 PBS Buffer Volume In μL | 3% $H_2O_2$ Volume In μL | Equivalence of $H_2O_2$ | Excess of $H_2O_2$ | Gelling Time |
|---|---|---|---|---|---|
| 2.5 mg | 166 μL | 33.2 μL (0.9 μL $H_2O_2$) | 26.4 | 25.4 | 38 Sec |
| 2.5 mg | 166 μL | 16.6 μL (0.45 μL $H_2O_2$) | 13.2 | 12.2 | 110 Sec |
| 2.5 mg | 166 μL | 8.3 μL (0.22 μL $H_2O_2$) | 6.6 | 5.6 | 4.20 min |
| 2.5 mg | 166 μL | 4.15 μL (0.11 μL $H_2O_2$) | 3.3 | 2.3 | 6.0 min |

B. Thiol Terminated Polymer and Maleimide Cross-Linker.

Another embodiment of the present invention includes hydogels of thiol terminated PEGs (e.g. 8-arm-PEG-SH) cross-linked with maleimide cross-linkers. The in situ forming hydrogel was obtained by mixing the solutions of the thiol terminated PEG and the cross-linker having a maleimide termination $BMPEO_3$ (bis-maleimido triethylene glycol) in phosphate buffer pH 5.38 and 7.4 to obtain the hydrogels. The hydrogel forms by the formation of the thioether bonds and gels almost instantaneously as shown in Table 4.

TABLE 4

Hydrogel (4% w/v) with $BM(PEO)_3$ as cross-linker

| S. No | 8-Arm-PEG-SH | $BM(PEO)_3$ wt | PB pH | Glycerin % | Gelling Time |
|---|---|---|---|---|---|
| 1 | 8 mg | 2 mg | 5.38 | 25 | 10 sec |
| 2 | 8 mg | 2 mg | 5.38 | 50 | 10 sec |
| 3 | 8 mg | 2 mg | 7.4 | 25 | 2 sec |
| 4 | 8 mg | 2 mg | 7.4 | 50 | 2 sec |

C. Sulfhydryl-Terminated Polymer and Thiopyridine Cross-Linker.

Yet another embodiment of the present invention is a gel based on the 4-arm-PEG-SH and 8-arm-PEG-SH cross-linked with 4-arm and 8-arm-PEG respectively having thiopyridine terminal groups. The thiol terminated PEG (4 and 8-arm PEG-SH) is treated with three fold excess of dithiodipyridine (aldrithiol) in alcohol under mild acidic conditions overnight at room temperature. The product, a thiopyridine terminated PEG (4 arm PEG-S-TP and 8-arm PEG-S-TP) so obtained is purified using the size exclusion chromatography. This PEG-S-TP product is used for the gel formation.

NMR for the thiopyridine terminated PEG.

PEG-SH: 1H-NMR ($CDCl_3$, 500 MHz) δ 3.50 (t, 2H, J=2, 4 Hz, $OCH_2$) 3.60-3.67 (m, nH, $OCH_2$—$CH_2$—O)

PEG-S-TP: 1H-NMR ($CDCl_3$, 500 MHz) δ 3.17 (t, 1H, J=2, 4 Hz, —CH—S-TP) 3.50 (t, 2H, J=2, 4 Hz, $OCH_2$) 3.60-3.67 (m, nH, $OCH_2$—$CH_2$—O), 3.8 (t, 1H, J=2, 4 Hz,

—CH—S-TP) 1H, J=2.4 Hz, Ar) 1H, J=2.6 Hz, Ar) 8.47 (d, 1H, J=3 Hz, Ar) 8.62 (d, 1H, J=3 Hz, Ar).

The in situ forming hydrogel was obtained by spraying the solution of the thiol terminated PEG and the cross-linker: having a thiopyridine termination developed in-house, from a dual barrel syringe to obtain the hydrogel. The solution of polymer and cross-linker were made in phosphate buffer pH 8. The formulation comprising PEG with 4 and 8 terminal thiol groups, respectively, was used for the formation of hydrogel as shown in Table 5. The thiopyridine terminated cross-linker was obtained from the 4- and 8-arm thiol terminated PEG, respectively, as also shown in Table 5.

TABLE 5

Hydrogel with PEG-S-TP as cross-linker

| S. No | Composition | Concentration of polymer (% w/v) | Ratio | Gelation Time |
|---|---|---|---|---|
| 1 | 4-arm-PEG-S-TP + 4-arm-PEG-SH | 8 | 1:1 | 15-30 sec |
|  |  | 6 | 1:1 | 15-30 sec |
|  |  | 5 | 1:1 | 15-30 sec |
| 2 | 8-arm-PEG-S-TP + 8-arm-PEG-SH | 8 | 1:1 | 15-30 sec |
|  |  | 6 | 1:1 | 15-30 sec |
|  |  | 5 | 1:1 | 15-30 sec |
| 3 | 8-arm-PEG-S-TP + 4-arm PEG-SH | 8 | 1:1 | 15 sec |
|  |  | 6 | 1:1 | 15 sec |
|  |  | 5 | 1:1 | 15 sec |
| 4 | 4-arm-PEG-S-TP + 8-arm PEG-SH | 8 | 1:1 | 15 sec |
|  |  | 6 | 1:1 | 15 sec |
|  |  | 5 | 1:1 | 15 sec |

The concentration of the polymer solution and the cross-linker was varied to yield the hydrogel almost instantaneously, as shown in Table 6. The hydrogel is obtained by the formation of the disulfide bridges either inter or intramolecular in the thiol terminated PEG.

Table 6

Hydrogel with PEG-S-TP as cross-linker (different ratios)
8-arm PEG-SH (compound A) + 8-arm PEG-S-TP (compound B)

| S. No | Compound % w/v | Ratio A:B | Gelling time |
|---|---|---|---|
| 1 | 8 | 1:1 | 20-30 sec |
| 2 | 8 | 2:1 | 20-30 sec |
| 3 | 8 | 1:2 | 20-30 sec |
| 4 | 6 | 1:1 | 30 sec |
| 5 | 6 | 2:1 | 30 sec |
| 6 | 6 | 1:2 | 30 sec |
| 7 | 5 | 1:1 | 30 sec |
| 8 | 5 | 2:1 | 30 sec |
| 9 | 5 | 1:2 | 30 sec |

Example 2

Adhesion

To enhance the adhesion of the gel to eye and the skin the cell adhesive component is incorporated in the gel. Accordingly, one of the embodiments of the present invention discloses the use of the peptide sequence, Arg-Gly-Asp (RGD), which is naturally present in many proteins involved in adhesion of cells to other cells and to basement membrane. As a result of better contact, this provides better transfer of a drug from the gel to the site of application. Furthermore, the presence of RGD sequences can be recognized by cellular receptors, thereby serving as attachment sites on the corneal epithelial cells or keratinocytes cells on the skin. The RGD is known to accelerate skin and wound repair.

RGD peptide comprising the 'Arg-Gly-Asp' sequence, such as the linear peptide Arg-Gly-Asp-Cys (SEQ ID NO. 1), Gly-Arg-Gly-Asp-Ser (SEQ. ID NO. 2), (Gly-Arg-Gly-Asp-Ser-Pro (SEQ ID NO. 3), or as the cyclic peptide Cyclo-Arg-Gly-Asp-Tyr-Lys (SEQ ID NO. 4), were used to enhance the adhesion of the gel on the cells and were synthesized as described below.

Synthesis of the RGD Derivatized PEG Cross-Linker:

Step 1: The thiol terminated PEG (8-arm PEG-SH) (Ig) was treated with three fold excess of dithiodipyridine (aldrithiol) (3 g) in alcohol (methanol, 20 ml) under mild acidic conditions overnight at room temperature.

Figure 10:
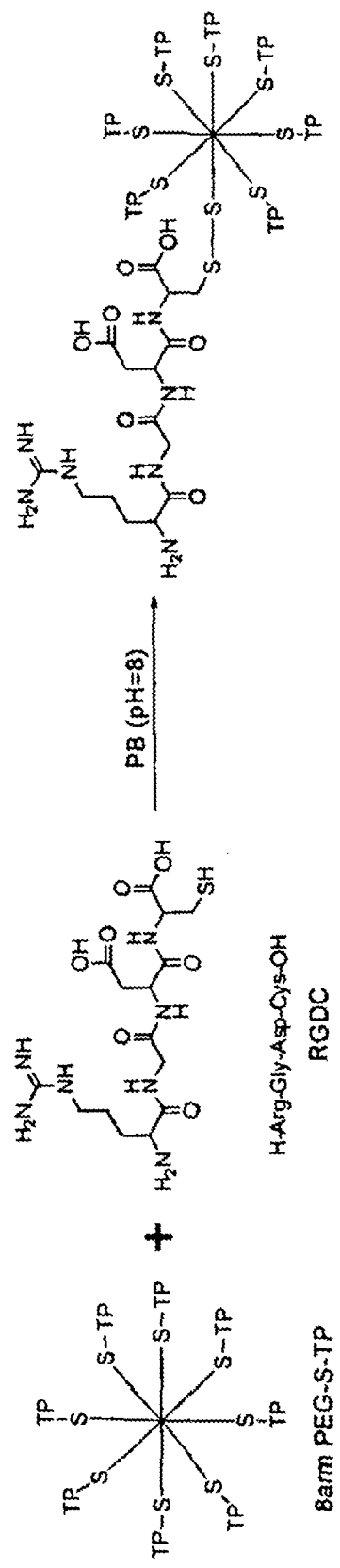
FIG. 10 depicts attaching the RGD peptide on the 8-arm-Peg-SH.

Step 2: The thiopyridine terminated PEG obtained from Step 1 was reacted with the RGD peptide having Arg-Gly-Asp-Cys sequence (FIG. 10). The thiopyridine terminated PEG was reacted with the RGD peptides in alcohol under mild basic conditions. The amount of RGD is taken proportional to the sites at which it is required to be appended e.g., the 8-arm PEG-TP (200 mg) was reacted with 1 equivalent of RGD to appended the RGD on one arm (36 mg), and the 8-arm PEG-TP (200 mg) was reacted with 3 equivalents of RGD (108 mg) to appended the RGD on three arms.

The hydrogel was obtained by spraying the solution of thiol terminated PEG (8-armPEG-SH) and the cross-linker consisting of PEG having partial thiopyridine and RGD terminal groups (RGDC-8-armPEG-S-TP), in phosphate buffer pH 8. The hydrogel composition is shown in Table 7.

TABLE 7

Hydrogel compositions having Adhesive RGD peptide

| S. No. | Polymers | % w/v of polymers in PB (pH 8) | Ratio | Gelling time |
|---|---|---|---|---|
| 1 | 8-armPEG-SH | 5 | 1:1 | ~10 min |
| 2 | + | 6 | 1:1 | ~10 min |
| 3 | RGDC-8-armPEG-STP (5 arm) | 8 | 1:1 | ~6 min |
| 4 | 8-armPEG-SH | 5 | 1:1 | ~6 min |
| 5 | + | 6 | 1:1 | ~5 min |
| 6 | RGDC-8-armPEG-STP (2 arm) | 8 | 1:1 | ~5 min |
| 7 | 8-armPEG-SH | 5 | 1:1 | ~4 min |
| 8 | + | 6 | 1:1 | ~3 min |
| 9 | RGDC-8-armPEG-STP (1 arm) | 8 | 1:1 | ~3 min |

In another embodiment of the invention, a spray-on hydrogel was obtained by spraying the solution of thiol terminated PEG (8-arm PEG-SH) and along with the cross-linker solution consisting of (a) thiopyridine terminated PEG (8-arm PEG-S-TP) and (b) PEG having partial thiopyridine and RGD terminal groups (RGDC-8-armPEG-S-TP). The solution of polymer and cross-linker were mixed in phosphate buffer pH 8. The hydrogel results instantaneously. The hydrogel compositions are shown in Table 8.

TABLE 8

Hydrogel compositions with Adhesive (RGD peptide)

| Polymer A | Polymer B | Polymer C | % w/v polymer A and (B + C) in PB (pH 8) | Ratio A:B + C | Ratio B:C | Gelling time |
|---|---|---|---|---|---|---|
| 8-armPEG-SH | RGDC-8-arm PEG-STP (5arm) | 8-arm PEG-STP | 5 | 1:1 | 1:1 | ~30-40 sec |
|  |  |  | 6 | 1:1 | 1:1 | ~30-40 sec |
| 8-armPEG-SH | RGDC-8-armPEG-STP (2arm) | 8-arm PEG-STP | 5 | 1:1 | 1:1 | ~30-40 sec |
|  |  |  | 6 | 1:1 | 1:1 | ~30-40 sec |
| 8-armPEG-SH | RGDC-8-arm PEG-STP (1arm) | 8-arm PEG-STP | 5 | 1:1 | 1:1 | ~30-40 sec |
|  |  |  | 6 | 1:1 | 1:1 | ~30-40 sec |

Example 3

Formulations with Additives

A spray-on hydrogel was obtained by dissolving the thiol terminated PEG (4-arm-PEG-SH and 8-arm PEG-SH) and the thiopyridine terminated PEG (4-arm-PEG-S-TP and 8-arm PEG-S-TP) (Formulation in accordance with Example 1c), and an additive comprising a solution of polyvinyl pyrrolidone (PVP) in phosphate buffer pH 8. The concentration of PVP was varied from 1.5-2% w/v as shown in Table 9.

TABLE 9

Hydrogel Compositions with additive PVP

| S. No | Compositions | Ratio of polymers | Conc. Of PVP (% w/v) | Conc. Of polymers (% w/v) |
|---|---|---|---|---|
| 1 | 4-arm-PEG-S-TP + 4-arm-PEG-SH | 1:1 | — | 5 |
|  | 8-arm-PEG-S-TP + 8-arm-PEG-SH | 1:1 | — | 5 |
|  | 8-arm-PEG-S-TP + 4-arm PEG-SH | 1:1 | — | 5 |
| 2 | 4-arm-PEG-S-TP + 4-arm-PEG-SH | 1:1 | 1.5 | 5 |
|  | 8-arm-PEG-S-TP + 8-arm-PEG-SH | 1:1 |  |  |
|  | 8-arm-PEG-S-TP + 4-arm PEG-SH | 1:1 |  |  |
| 3 | 4-arm-PEG-S-TP + 4-arm-PEG-SH | 1:1 | 2 | 5 |
|  | 8-arm-PEG-S-TP + 8-arm-PEG-SH | 1:1 |  |  |
|  | 8-arm-PEG-S-TP + 4-arm PEG-SH | 1:1 |  |  |

Two spray-on hydrogels were obtained by dissolving the thiol terminated PEG (8-arm PEG-SH) and the thiopyridine terminated PEG (8-arm PEG-S-TP) (in accordance with a formulation of Example 1c) with additives comprising (a) a solution of 2% w/v polyvinylpyrrolidone (PVP) and 5% v/v of glycerin in phosphate buffer pH 8, and (b) by solution of 2% w/v polyvinyl pyrrolidone (PVP), 5% v/v of glycerin and 5% v/v of polyethylene glycol (MW 600) in phosphate buffer pH 8. These are shown in Table 10.

TABLE 10

Hydrogel Compositions with additive Glycerin and PEG (MW 600)

| S. No 1 | Compositions | Ratio of polymers | Conc. Of 8 arm PEG (MW 20,000) (% w/v) | Conc. Of Glycerin (% v/v) |
|---|---|---|---|---|
|  | 8-arm-PEG-S-TP + 8-arm-PEG-SH Dissolved in Phosphate buffer pH 8 containing PVP (2% w/v)) | 1:1 | 6 | 5 |

| S. No 2 | Compositions | Ratio of polymers | Conc. Of 8 arm PEG (MW 20,000) (% w/v) | Conc. Of PEG (MW 600) (% v/v) (+ Glycerin 5% v/v) |
|---|---|---|---|---|
|  | 8-arm-PEG-S-TP + 8-arm-PEG-S H Dissolved in Phosphate buffer pH 8 containing PVP (2% w/v) | 1:1 | 6 | 5 |

A spray-on hydrogel was obtained by dissolving the thiol terminated PEG (4-arm-PEG-SH and 8-arm PEG-SH) and the thiopyridine terminated PEG (4-arm-PEG-S-TP and 8-arm PEG-S-TP) in a solution of polyvinylpyrrolidone (PVP) and hydroxypropyl methylcellulose (HPMC) in phosphate buffer pH 8. The concentration of PVP was varied from 1.5-2% w/v as shown in Table 11.

TABLE 11

Hydrogel Compositions with additives PVP and HPMC

| S. No | Compositions | Ratio of polymers | Conc. Of PVP (% w/v) | Conc. Of HPMC (% w/v) | Conc. Of polymers (% w/v) |
|---|---|---|---|---|---|
| 1 | 4-arm-PEG-S-TP + 4-arm-PEG-SH | 1:1 | 1.5 | 0.5 | 5 |
|  | 8-arm-PEG-S-TP + 8-arm-PEG-SH | 1:1 |  |  |  |
|  | 8-arm-PEG-S-TP + 4-arm PEG-SH | 1:1 |  |  |  |
| 2 | 4-arm-PEG-S-TP + 4-arm-PEG-SH | 1:1 | 2 | 1.0 | 5 |
|  | 8-arm-PEG-S-TP + 8-arm-PEG-SH | 1:1 |  |  |  |
|  | 8-arm-PEG-S-TP + 4-arm PEG-SH | 1:1 |  |  |  |

Example 5

Formulations Including Drug

A. Lidocaine and Doxycycline Hyclate.

The drugs Lidocaine and Doxycycline Hyclate were incorporated in the hydrogel by dissolving the drugs in the polymer solution (8-arm PEG-SH) as shown in Table 12. The drug incorporated polymer solution was cross-linked using the thiopyridine terminated PEG (8-arm PEG-S-TP) in phosphate buffer pH 8. Also, The drug incorporated polymer solution was cross-linked using the thiopyridine terminated PEG (8-arm PEG-S-TP) in a solution of 2% w/v polyvinyl pyrrolidone (PVP) and 5% v/v of glycerin in phosphate buffer pH 8 as shown in Table 12.

TABLE 12

Hydrogel Compositions with Doxycycline Hyclate, Lidocaine HCL and Benzalkonium Chloride

| S. No | Compositions | Ratio of polymers | Conc. Of PEG (% w/v) | Drugs % w/v |
|---|---|---|---|---|
| 1 | 8-arm-PEG-S-TP + 8-arm-PEG-SH (Dissolved in phosphate buffer pH 8) | 1:1 | 6 | 2.5% Lidocaine HCL and 0.15% Benzalkonium HCL |
| 2 | 8-arm-PEG-S-TP + 8-arm-PEG-SH Dissolved in Phosphate buffer pH 8 containing Other additives: PVP (2% w/v) PEG Mw 600 (5% v/v) Glycerin (5% v/v) | 1:1 | 6 | 2.5% Lidocaine HCL and 0.15% Benzalkonium HCL |
| 3 | 8-arm-PEG-S-TP + 8-arm-PEG-SH (Dissolved in phosphate buffer pH 8) | 1:1 | 8 | 0.34% Doxycycline hyclate |
| 4 | 8-arm-PEG-S-TP + 8-arm-PEG-SH Dissolved in Phosphate buffer pH 8 containing Other additives: PVP (2% w/v) PEG Mw 600 (5% v/v) Glycerin (5% v/v) | 1:1 | 8 | 0.34% Doxycycline hyclate |

B. Doxycycline

In another embodiment, the drug Doxycycline Hyclate was incorporated in the hydrogel by dissolving the drug in the polymer (8-arm-PEG-SH) solution in phosphate buffer pH 8. The drug incorporated polymer solution was cross-linked using the $H_2O_2$ solution as shown in Table 13.

TABLE 13

Hydrogel compositions cross-linked by $H_2O_2$ with Doxycycline Hyclate

| Wt of 8-arm-PEG-SH (mg) | pH = 8 PBS Buffer Volume In μL | 3% $H_2O_2$ Volume In μL | Equivalent of $H_2O_2$ | Doxycycline Hyclate % w/v |
|---|---|---|---|---|
| 8 mg | 200 μL | 1.8 μL | 0.5 | 0 |
| 8 mg | 200 μL | 1.8 μL | 0.5 | 0.5 |
| 8 mg | 200 μL | 1.8 μL | 0.5 | 0.25 |
| 8 mg | 200 μL | 1.8 μL | 0.5 | 0.12 |
| 12 mg | 200 μL | 5.4 μL | 0.5 | 0.5 |
| 12 mg | 200 μL | 5.4 μL | 0.5 | 0.25 |
| 12 mg | 200 μL | 5.4 μL | 0.5 | 0.122 |
| 12 mg | 200 μL | 5.4 μL | 0.5 | 0.061 |
| 16 mg | 200 μL | 5.4 μL | 0.5 | 0.5 |
| 16 mg | 200 μL | 5.4 μL | 0.5 | 0.25 |
| 16 mg | 200 μL | 5.4 μL | 0.5 | 0.122 |

C. Indomethacin.

The drug indomethacin was incorporated in the hydrogel by dissolving the drug in the polymer solution (8-arm PEG-SH) as shown in Table 14. The drug incorporated polymer solution was cross-linked using the thiopyridine terminated PEG (8-arm PEG-S-TP) in phosphate buffer pH 8. Also, The drug incorporated polymer solution was cross-linked using the thiopyridine terminated PEG (8-arm PEG-S-TP) in a solution of 2% w/v polyvinylpyrrolidone (PVP) and 5% v/v of glycerin in phosphate buffer pH 8 as shown in Table 14.

Synthesis of the RGD Linked to Indomethacin

Step 1: The RGD peptide having sequence Arg-Gly-Asp-Cys (SEQ ID NO. 1) was treated with three fold excess of dithiodipyridine (aldrithiol) in alcohol under mild acidic conditions overnight at room temperature. To obtain the protected peptide.

Step 2: The indomethacin (1 eq) would be linked thiopyridine protected peptide (1 eq) in the presence of coupling agents coupling agents 4-dimethylaminopyridine and 1(3-dimethylaminopropyl) 3-ethylcarbodiimide (1 eq) in solution of dry dimethylformamide and using hydroxyl-terminated PEG as a spacer. The reaction would be carried out overnight at room temperature and the product would be separated by size exclusion chromatography using Sephadex LH 60 packing. The indomethacin-PEG-RGD conjugate would be linked to the 8-arm PEG-SH through the disulfide bond formation at the cysteine terminal of the peptide in phosphate buffer (pH 7.4) with stirring overnight and the product would be obtained by lyophilization of the reaction mixture for 12-24 hrs.

TABLE 14

Hydrogel Compositions with Indomethacin

| S. No | Compositions | Ratio of polymers | Conc. Of PEG (% w/v) | Drugs % w/v |
|---|---|---|---|---|
| 1 | 8-arm-PEG-S-TP + 8-arm-PEG-SH (Dissolved in phosphate buffer pH 8) | 1:1 | 6 | 0.4% Indomethacin |
| 2 | 8-arm-PEG-S-TP + 8-arm-PEG-SH Dissolved in Phosphate buffer pH 8 containing Other additives: PVP (2% w/v) PEG Mw 600 (5% v/v) Glycerin (5% v/v) | 1:1 | 6 | 0.4% Indomethacin |

D. Doxycycline Conjugatd to RGD.

Doxycycline-RGD-PEG was incorporated in the hydrogel by dissolving the same in the polymer solution (8-arm PEG-SH) as shown in Table 15. The drug incorporated polymer solution was cross-linked using the thiopyridine terminated PEG (8-arm PEG-S-TP) in phosphate buffer pH 8. Also, The drug incorporated polymer solution was cross-linked using the thiopyridine terminated PEG (8-arm PEG-S-TP) in a solution of 2% w/v polyvinylpyrrolidone (PVP) and 5% v/v of glycerin in phosphate buffer pH 8 as shown in Table 15. The Doxycycline-RGD-PEG component was synthesized and the synthetic procedure is given below.

Synthesis of the RGD-Linked Drug Composition

Step 1: The RGD peptide having sequence Arg-Gly-Asp-Cys was treated with three fold excess of dithiodipyridine (aldrithiol) in alcohol under mild acidic conditions overnight at room temperature. To obtain the protected peptide Step 2: The Doxycycline (1 eq) was linked thiopyridine protected peptide (1 eq) in the presence of coupling agents 4-dimethylaminopyridine and 1(3-dimethylaminopropyl)3-ethylcarbodiimide (1 eq) in solution of dry dimethylformamide. The reaction was carried out overnight at room temperature and the product was separated by size exclusion chromatography using Sephadex LH 60 packing. The PEGylation of Doxycycline-RGD conjugate was carried out using 8-arm PEG-SH in phosphate buffer (pH 7.4) with stirring overnight. The ratio of Doxycycline-RGD to 8-arm PEG-SH was taken (1:1 per arm). The Doxycycline-RGD-PEG so synthesized was obtained by lyophilization of the reaction mixture for 12-24 hrs.

The different sizes of PEG (10-20 KDa) and with different number of thiol termination (2, 4 and 8-arm Peg-SH) can be used. Further, the amount of Doxycycline-RGD can be taken proportional to the number of arms/sites at which it is required to be appended on the 4 or 8-arm PEG-SH.

TABLE 15

Hydrogel Compositions with Doxycycline-RGD-PEG

| S. No | Compositions | Ratio of polymers | Conc. Of PEG (% w/v) | Drugs % w/v |
|---|---|---|---|---|
| 1 | 8-arm-PEG-S-TP + 8-arm-PEG-SH (Dissolved in phosphate buffer pH 8) | 1:1 | 6 | Doxycycline-RGD-PEG (equivalent to 0.34%) |
| 2 | 8-arm-PEG-S-TP + 8-arm-PEG-SH Dissolved in Phosphate buffer pH 8 containing Other additives: PVP (2% w/v) PEG Mw 600 (5% v/v) Glycerin (5% v/v) | 1:1 | 6 | Doxycycline-RGD-PEG (equivalent to 0.34%) |

The different sizes of PEG (10-20 KDa) and with different number of thiol termination (2, 4 and 8-arm Peg-SH) can be used. Further, the amount of indomethacin-PEG-RGD can be taken proportional to the number of arms/sites at which it is required to be appended on the 4 or 8-arm PEG-SH.

E. Olvanil.

The drug olvanil was be incorporated in the hydrogel by dispersing the drug in the polymer solution (8-arm PEG-SH). The drug incorporated polymer solution was cross-linked using the thiopyridine terminated PEG (8-arm PEG-S-TP) in phosphate buffer pH 8. Also, the drug incorporated polymer solution was cross-linked using the thiopyridine terminated PEG (8-arm PEG-S-TP), both the polymer and cross-linker were dissolved in a solution of 2% w/v polyvinylpyrrolidone (PVP) and 5% v/v of glycerin in phosphate buffer pH 8 as shown in Table 15.

The PEG-Olvanil-Cysteine was incorporated in the hydrogel by dissolving the same in the polymer solution (8-arm PEG-SH). The drug incorporated polymer solution was cross-linked using the thiopyridine terminated PEG (8-arm PEG-S-TP) in phosphate buffer pH 8. Also, the drug incorporated polymer solution was cross-linked using the thiopyridine terminated PEG (8-arm PEG-S-TP) in a solution of 2% w/v polyvinylpyrrolidone (PVP) and 5% v/v of glycerin in phosphate buffer pH 8.

The PEG-Olvanil-Cysteine component was synthesized and the synthesis procedure is given below.

Synthesis of the PEG-Olvanil-Cysteine

Step 1: The 3-fold excess of Fmoc-Cysteine(S-Trt)-COOH was reacted with Olvanil in presence of diisopropylcarbodiimide under basic conditions by adding pyridine in dimethyl formamide. The formation of the Olvanil-Cysteine product was analyzed using ESI-MS.

Step 2: Olvanil-Cys(trt) ester was linked to 5 kDa-PEG-NHS in the presence of N N-Diisopropylethylamine by dissolving in dimethyl formamide by stirring overnight. The product so obtained was purified by Size exclusion chromatography using G-25 Sephadex beads. The formation of the product was analyzed using MALDI-TOF.

Example 6

Drug Delivery

One of the embodiments of the present invention includes a therapeutic agent or drug, such as lidocaine (a topical anesthetic), benzalkonium chloride (a topical antiseptic), olvanil (an anti-inflammatory agent), doxycycline (an antibiotic), pilocarpine or protease inhibitors incorporated into the hydrogel composition.

Formulations incorporating the drugs into the hydrogel composition are shown in Tables 12-15. For prolonged retention of drugs at the site of application, drugs linked to RGD peptide appended onto PEG were incorporated in the hydrogel composition, e.g., doxycycline as disclosed in Example 5.D. The RGD peptide, comprising the 'Arg-Gly-Asp' sequence, such as the liner peptide or the cyclic peptides are disclosed. The examples of the linear peptide include Arg-Gly-Asp-Cys (SEQ ID NO. 1), Gly-Arg-Gly-Asp-Ser (SEQ ID NO. 2), Gly-Arg-Gly-Asp-Ser-Pro (SEQ ID NO. 3), and the cyclic peptide include, Cyclo-Arg-Gly-Asp-Tyr-Lys (SEQ ID NO. 4) but are not so limited, and can be extended to any peptide having the sequence 'Arg-Gly-Asp'. These prodrugs are designed to provide cell adhesive and retentive properties to enhance binding to corneal epithelial cells or to the extracellular matrix of the injured skin for slow-release the active drug.

Example 7

Reversible Cross-Links

The reversible nature of the disulfide bridges to enable easy wash-off of the gel was established in-vitro and in-vivo using a solution of reducing agent like Glutathione. The concentration of Glutathione was varied from 1-5% w/v in phosphate buffer pH 8. The hydrogels having the varied compositions are shown in Table 16 and they showed a reversible nature of the disulfide linkages resulting in the hydrogel to convert from gel to sol. The hydrogel having a composition 6% w/v of 8-arm-PEG-SH and 8-arm-PEG-S-TP was sprayed on the mice and thereafter the hydrogel was washed off using a solution of Glutathione having a concentration 5% w/v.

TABLE 16

Evaluation of concentration of Glutathione required
to reverse the disulfide cross-links in hydrogel

| S. No | Composition | Ratio of polymers | Conc. Of polymers (% w/v) | Conc. of Glutathione (% w/v) | | |
|---|---|---|---|---|---|---|
| | | | | 1 | 3 | 5 |
| 1 | 4-arm-PEG-S-TP + 4-arm-PEG-SH | 1:1 | 5 | 30 min | 20 min | 10-15 min |
| | | 1:1 | 6 | 30 min | 20-25 min | 15 min |
| | | 1:1 | 8 | 40-45 min | 25-30 min | 15-20 min |
| 2 | 8-arm-PEG-S-TP + 8-arm-PEG-SH | 1:1 | 5 | 40-45 min | 20-25 min | 15 min |
| | | 1:1 | 6 | Not investigated | 20-25 min | 15-20 min |
| | | 1:1 | 8 | Not investigated | 30-35 min | 15-20 min |
| 3 | 8-arm-PEG-S-TP + 4-arm PEG-SH | 1:1 | 5 | 35-40 min | 15 min | 10-12 min |
| | | 1:1 | 6 | Not investigated | 15-20 min | 10-12 min |
| | | 1:1 | 8 | Not investigated | 15-20 min | 10-15 min |
| 4 | 4-arm-PEG-S-TP + 8-arm PEG-SH | 1:1 | 5 | 30-40 min | 15 min | 10-12 min |
| | | 1:1 | 6 | Not investigated | 15 min | 10-12 min |
| | | 1:1 | 8 | Not investigated | 20-30 min | 15 min |

By exposure to or application of a reducing agent, such as cysteine or glutathione, to the cross-linked hydrogel composition, the composition can be completely dissolved and washed away. One of the embodiments of the present invention is to show the reversible nature of the cross-links and easy wash off of the gel. This is exemplified in the present invention using the normal skin of mice and using in vitro experiments.

Example 7

Physical Properties

A preferred hydrogel composition of the subject invention must be strong and flexible. It should not dry out too fast nor swell/shrink excessively. These properties were tested using rheology instrumentation and manual inspection of the gel. One of the embodiments of the present invention comprises 0.2-5% w/v polyvinyl pyrolidone (PVP), 0.2-5% w/v cellulose derivatives, such as hydroxypropyl methylcellulose, hydroxypropyl cellulose, 0.5-5% v/v PEG (6000 Da) and 0.4-25% v/v glycerin. Other additives that can be included in the hydrogel composition include phospholipids such as soybean phospholipids, eggyolk phospholipids, lecithins, soy lecithins, sphingomyelins, phosphatidylcholine, phosphatidylglycerol, phosphatidic acid, phosphatidylethanolamine, phosphatidyl serines, and PEG-ylated phospholipids. When sprayed on a Petri dish, this formulation produces a gel that forms a uniform layer without running of excess liquid (FIG. 9). The gel may be peeled from the dish without tearing. Furthermore, the gel appears to be useful for up to 4 days. Based on these physical properties, a gel having a formulation as shown in Tables 9 or 10 or 11 may serve as the entire wound dressing when applied to skin, obviating the use of a gauze bandage.

Rheological measurements were performed on a 4 and 6% w/v gel of 8-arm PEG-SH cross-linked by $H_2O_2$ using a Rheometrics rheometer using RSI orchestrator software at 37° C. with cone plate geometry (plate diameter of 25 mm, gap of 3 mm and 2° angle). Samples were equilibrated on the plate for 5 min to reach the running temperature before each measurement. All rheological determinations were made at least in triplicate for each hydrogel using separate samples. Rheological test parameters like storage/elasticity (G') and loss (G") moduli were obtained under dynamic conditions of non-destructive oscillatory tests. The hydrogels of 8-arm Peg-SH and $H_2O_2$ formed in phosphate buffer and phosphate buffer containing 2% w/v polyvinyl pyrrolidone, 5% v/v glycerin and 5% v/v polyethylene glycol (MW 600) was measured. The results for the rheology are shown in FIG. 15.

Additional rheological measurements were performed on a 5% w/v gel of 8-arm PEG-SH cross-linked by 8-arm PEG-S-TP using a Rheometrics rheometer using RSI orchestrator software at 37° C. with cone plate geometry (plate diameter of 25 mm, gap of 3 mm and 2° angle). Samples were equilibrated on the plate for 5 min to reach the running temperature before each measurement. All rheological determinations were made at least in triplicate for each hydrogel using separate samples. Rheological test parameters like storage/elasticity (G') and loss (G") moduli were obtained under dynamic conditions of non-destructive oscillatory tests. The hydrogels of 8-arm PEG-SH cross-linked by 8-arm PEG-S-TP formed in phosphate buffer and phosphate buffer containing 2% w/v polyvinyl pyrrolidone, 5% v/v glycerin and 5% v/v polyethylene glycol (MW 600) was measured.

The invention claimed is:

1. A wound dressing, comprising
a first component comprising an eight arm hydrophilic polymer with thiol terminated ends; and
a second component comprising a cross-linker, said cross-linker comprising a thiopyridine terminated polyethylene glycol and forming reversible disulfide cross-linkages with the thiol terminated ends of the hydrophilic polymer;
wherein the first and second components react to form a uniform layer that adheres to skin of a mammal and acts as a wound dressing.

2. The wound dressing of claim 1, wherein the polymer is polyethylene glycol.

3. The wound dressing of claim 1, wherein the wound dressing further comprises a drug or a combination of drugs.

4. The wound dressing of claim 2 wherein the polyethylene glycol is derivatized to contain peptide comprising RGD.

5. The wound dressing of claim 4 wherein a drug or drugs are conjugated to the peptide comprising RGD.

6. The wound dressing of claim 4 wherein the peptide comprising RGD further comprises cysteine.

7. The wound dressing of claim 4 wherein the peptide comprising RGD is a linear peptide having an amino acid sequence selected from the group consisting of Arg-Gly-Asp-Cys, Gly-Arg-Gly-Asp-Ser, and Gly-Arg-Gly-Asp-Ser-Pro SEQ ID NO. 1, SEQ ID NO. 2, and SEQ ID NO. 3.

8. The wound dressing of claim 1 wherein the thiopyridine terminated polyethylene glycol is obtained by reacting the 2-dithiopyridine or 4-dithiopyridine with thiol terminated polyethylene glycol.

9. The wound dressing of claim 1, wherein the wound dressing further comprises at least one additive selected from the group consisting of polyvinyl pyrrolidone, polyethylene oxide, cellulose derivatives, 0.2%-5% cellulose, 0.4-25% v/v glycerin, propylene glycol, 0.5-5% v/v PEG in the range of 100-10000 Da, propylene glycol, and phospholipids.

10. The wound dressing of claim 1 wherein the wound dressing provides controlled release of a drug.

11. An ocular dressing, comprising
a first component comprising an eight arm hydrophilic polymer with thiol terminated ends; and
a second component comprising a cross-linker, said cross-linker comprising a thiopyridine terminated polyethylene glycol and forming reversible disulfide cross-linkages with the thiol terminated ends of the hydrophilic polymer;
wherein the first and second components react to form a uniform layer that adheres to the ocular surface of an eye of a mammal.

12. The ocular dressing of claim 11 wherein the ocular dressing comprises a drug or combination of drugs for topical administration of the drug or drugs to the eye.

13. The ocular dressing of claim 11, wherein the polymer is polyethylene glycol.

14. The ocular dressing of claim 13 wherein the polyethylene glycol is derivatized to contain a peptide comprising RGD.

15. The ocular dressing of claim 14 wherein a drug or drugs are conjugated to the peptide comprising RGD.

16. The ocular dressing of claim 14 wherein the peptide comprising RGD further comprises cysteine.

17. The ocular dressing of claim 14 wherein the peptide comprising RGD is a linear peptide having an amino acid sequence selected from the group consisting of Arg-Gly-Asp-Cys, Gly-Arg-Gly-Asp-Ser, and Gly-Arg-Gly-Asp-Ser-Pro SEQ ID NO. 1, SEQ ID NO. 2, and SEQ ID NO. 3.

18. The ocular dressing of claim 11 wherein the thiopyridine terminated polyethylene glycol is obtained by reacting the 2-dithiopyridine or 4-dithiopyridine with thiol terminated polyethylene glycol.

19. The ocular dressing of claim 11, wherein the ocular dressing further comprises at least one additive selected from the group consisting of polyvinyl pyrrolidone, polyethylene oxide, cellulose derivatives, 0.2%-5% cellulose, 0.4-25% v/v glycerin, propylene glycol, 0.5-5% v/v PEG in the range of 100-10000 Da, propylene glycol, and phospholipids.

20. The ocular dressing of claim 11 wherein the ocular dressing provides controlled release of said a drug.

21. A drug delivery device for delivering drug for treatment of the eye, said drug delivery device comprising the ocular dressing of claim 11.

22. The dressing of claim 3 or wherein said drug or combination of drugs are selected from the group consisting of a topical anesthetic, antibiotic, antiseptic, analgesic, anti-inflammatory and a wound healing therapeutic agent.

23. The dressing of claim 22 wherein the drug is lidocaine, benzocaine, butamben, dibucaine, oxybuprocaine, pramoxine, proparacaine, proxymetacaine, novocaine, procaine, tetracaine, doxycycline, minocycline, oxytetracycline, sancycline, dedimethylamino tetracycline, indomethacin, diclofenac, ibuprofen, naproxen, ketoprofen, dexamethasone, a vallinoid, olvanil, capsaicin, benzalkonium chloride, an antiglaucoma medication, pilocarpine, timolol, levobunolol, betaxolol, or carbacol.

24. The dressing of claim 1 or 11 wherein the dressing further comprises a growth factor.

25. The dressing of claim 24 wherein the growth factor is selected from the group consisting of a cytokine, epidermal growth factor (EGF), an EGF protein having one or more repeats of the conserved amino acid sequence: CX7CX4-5CX10-13CXCX8GXRC (where X represents any amino acid), transforming growth factor alpha (TGF-alpha), transforming growth factor beta (TGF-b), keratinocyte growth factor (KGF-2), fibroblast growth factor, fibronectin, fibrinogen, Granulocyte-Monocyte Colony Stimulating Factor (GM-CSF) and platelet-derived growth factor (PDGF).

26. The dressing of claim 1 or 11 wherein the dressing is bioadhesive.

27. The dressing of claim 1 or 11 wherein the ratio of the first component to the second component is in the range of about 5:1 to 1:5 w/w.

28. The dressing of claim 1 or 11 wherein the first component are provided as a solution having a concentration of less than 30% w/v.

29. A wound or ocular dressing kit, comprising
   a first component comprising an eight arm hydrophilic polymer with thiol terminated ends;
   a second component comprising a cross-linker comprising a thiopyridine terminated polyethylene glycol and forming a reversible disulfide cross-linkage with the thiol terminated ends of the hydrophilic polymer, and
   a reducing agent in a solution separate from the first component and the second component to reverse the cross-linkage,
   wherein said first and second components being supplied as separate solutions and react when mixed together during administration to a wound site such that a reversible cross-linked gel matrix forms as a wound dressing on the surface of the wound in less than about 30 minutes.

30. The kit of claim 29 further comprising a drug, a growth factor, or both.

31. The kit of claim 29 further comprising a reducing agent for reversing the reversible cross-links of the formed hydrogel for dissolution and removal of the dressing from a wound.

32. The kit of claim 29, wherein the reducing agent is selected from the group consisting of cysteine and derivatives thereof, cysteine ethyl ester, cysteine methyl ester, glutathione, cysteine hydrocholoride, dithiothretol, N-Ethylmalemide, phosphine derivatives tetrakis-hydroxymethyl phosphonium chloride and tris-diethylaminomethyl phosphine trialkylphosphine agents, such as Tris[2-carboxyethyl] phosphine and mercaptoethanols, 2,3-dimercapto-1-propanol, dinitrobenzoic acid, a thiol, a mercaptan, a sulfite or bisulfate or ammonium or sodium salts thereof, thioglycolic acid, thiolactic acid, cysteine, thioglycerol, thioglycolic hydrazide, thioglycolamide, glycerol monothioglycolate, beta-mercapto-propionic acid, N-hydroxyethyl mercapto-acetamide, N-methyl mercapto-acetamide, beta-mercapto-ethylamine, beta-mercapto-propionamide, 2-mercapto-ethanesulfonic acid, dimercapto-adipic acid, dithiothreitol, homocysteinethiolactone, and a polythiol derivative formed by the addition of cysteamine onto a maleic anhydride-alkylvinylether copolymer.

33. The kit of claim 32, wherein the reducing agent is glutathione in a solution 1-5% w/v solution.

34. The dressing of claim 23, wherein the drug is butamben, dibucaine, oxybuprocaine, pramoxine, proparacaine, proxymetacaine, novocaine, procaine, tetracaine, doxycycline, minocycline, oxytetracycline, sancycline, dedimethylamino tetracycline, indomethacin, diclofenac, naproxen, ketoprofen, dexamethasone, avallinoid, olvanil, capsaicin, benzalkonium chloride, pilocarpine, timolol, levobunolol, betaxolol, or carbacol.

35. A wound dressing, comprising
   a first component comprising an eight arm hydrophilic polymer with thiol terminated ends;
   a second component comprising a cross-linker, said cross-linker comprising a thiopyridine terminated polyethylene glycol and forming reversible disulfide cross-linkages with the thiol terminated ends of the hydrophilic polymer; and
   a third component comprising at least one additive selected from the group consisting of 1.5-2% w/v polyvinyl pyrrolidone, 0.2%-5% cellulose, 0.5-5% v/v PEG in the range of 100-10000 Da, and 0.4-25% v/v glycerin;
   wherein the first, second and third components are capable of forming a uniform layer that adheres to skin of a mammal and acts as a wound dressing.

* * * * *

UNITED STATES PATENT AND TRADEMARK OFFICE
CERTIFICATE OF CORRECTION

PATENT NO. : 9,211,358 B2
APPLICATION NO. : 12/450995
DATED : December 15, 2015
INVENTOR(S) : Sinko et al.

It is certified that error appears in the above-identified patent and that said Letters Patent is hereby corrected as shown below:

On the title page

Item [75], delete "Siva Naga Sree Priay Anumolu" and insert --Siva Naga Sree Priya Anumolu--;

Item [60], delete "61/925,910" and insert --60/925,910--.

Signed and Sealed this
Tenth Day of May, 2016

Michelle K. Lee
*Director of the United States Patent and Trademark Office*

SEQUENCE LISTING

<160> NUMBER OF SEQ ID NOS: 4

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

```
Gly Arg Gly Asp Cys
1               5

<210> SEQ ID NO 2
<211> LENGTH: 5
<212> TYPE: PRT
<213> ORGANISM: Artificial
<220> FEATURE:
<223> OTHER INFORMATION: Synthetic

<400> SEQUENCE: 2

Gly Arg Gly Asp Ser
1               5

<210> SEQ ID NO 3
<211> LENGTH: 6
<212> TYPE: PRT
<213> ORGANISM: Artificial
<220> FEATURE:
<223> OTHER INFORMATION: Synthetic

<400> SEQUENCE: 3

Gly Arg Gly Asp Ser Pro
1               5

<210> SEQ ID NO 4
<211> LENGTH: 5
<212> TYPE: PRT
<213> ORGANISM: Artificial
<220> FEATURE:
<223> OTHER INFORMATION: Synthetic

<400> SEQUENCE: 4

Arg Gly Asp Tyr Lys
1               5
```